United States Patent [19]

Saito et al.

[11] Patent Number: 5,100,578

[45] Date of Patent: Mar. 31, 1992

[54] 2,5-DIPHENYLPYRIMIDINE COMPOUND

[75] Inventors: Shinichi Saito; Kouji Ohno; Hiromichi Inoue, all of Chiba, Japan

[73] Assignee: Chisso Corporation, Ohsaka, Japan

[21] Appl. No.: 426,227

[22] Filed: Oct. 25, 1989

[30] Foreign Application Priority Data

Oct. 31, 1988 [JP] Japan .................. 63-275851

[51] Int. Cl.$^5$ .................. C09K 19/34; C07D 239/02
[52] U.S. Cl. .................. 252/299.61; 544/298; 544/335
[58] Field of Search .................. 544/298, 335; 252/299.61, 299.01

[56] References Cited

U.S. PATENT DOCUMENTS

| | | | |
|---|---|---|---|
| 4,834,904 | 5/1989 | Krause et al. | 252/299.01 |
| 4,892,393 | 1/1990 | Terashima et al. | 252/299.61 |
| 4,900,472 | 2/1990 | Miyazawa et al. | 252/299.61 |
| 4,900,473 | 2/1990 | Miyazawa et al. | 252/299.61 |
| 4,911,863 | 3/1990 | Sage et al. | 252/299.65 |

FOREIGN PATENT DOCUMENTS 8705012 8/1987 World Int. Prop. O. ....... 252/299.6

Primary Examiner—John S. Maples
Assistant Examiner—Philip Tucker
Attorney, Agent, or Firm—Wenderoth, Lind & Ponack

[57] ABSTRACT

An optically active compound having a large spontaneous polarization ps value (ps) particularly for realizing a high speed response, and a liquid crystal composition are provided, which compound is an optically active 2,5-diphenylpyrimidine compound expressed by the formula

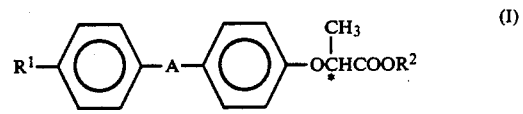

wherein $R^1$ is 1-20C alkyl or alkoxy, $R^2$ is 1-20C alkyl, A is

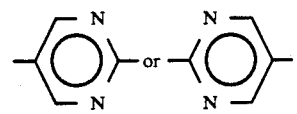

and * indicates an asymmetric carbon atom.

7 Claims, No Drawings

2,5-DIPHENYLPYRIMIDINE COMPOUND

BACKGROUND OF THE INVENTION

1. Field of the Invention

This invention relates to a novel organic compound and a liquid crystal composition containing the same. More particularly it relates to an optically active compound having an optically active group, a liquid crystal composition containing the same, and an electrooptical device using the composition.

2. Description of the Related Art

Liquid crystal display devices having superior specific features such as low voltage operation, small power consumption, flat panel display, etc. have recently been broadly used for television, computer terminal, particularly display terminal of movable goods, not to mention watches, electronic calculator, instruments, etc. Most of these goods have been employing TN (twist nematic) display mode. Further, STN mode having improved TN mode by increasing the twist angle to 180°–270° has also been gradually employed. These display modes are inferior in the aspect of response time to emissive mode display devices such as cathode ray tube, electroluminescence, plasma display, etc. Thus, various efforts of improvement have been made, but a TN mode device of high speed response has not yet been realized. However, in the case of a novel display mode using ferroelectric liquid crystals, the research on which has recently been actively developed, the response time has been notably shortened (Clark et al, Applied Phys. lett., 36, 899 (1980)). This display mode is directed to a method utilizing chiral smectic phases such as chiral smectic C phase (hereinafter abbreviated to SC*), etc. exhibiting ferroelectricity. It has been known that phases exhibiting ferroelectricity are not only SC* phase, but also chiral smectic F, chiral smectic G, chiral smectic H, chiral smectic I, etc.

Practical ferroelectric liquid crystal materials are liquid crystal compositions obtained by mixing a plurality of liquid crystal compounds or non-liquid crystal compounds, and a further improvement in material characteristics thereof has been required.

Such liquid crystal materials are not only those composed only of ferroelectric liquid crystal compounds, but also the materials may be composed by adding at least one kind of optically active substances to compounds or compositions exhibiting achiral smectic C, F, G, H, I or the like phase (hereinafter abbreviated to SC or the like phase), as basic substances. However, such optically active substances are preferred to exhibit liquid crystal phases, preferably ferroelectric liquid crystal phases. Even in the case that the substances exhibit no liquid crystal phases, the substances are preferred to have a structure similar to those of liquid crystal compounds, that is, to be quasi liquid crystal substances.

The ferroelectric liquid crystal display mode makes it possible to realize a response speed hundreds of times to thousands of times as quick as that of TN mode, and to exhibit memory effect due to bistability; thus various use applications of the mode including television having a flat panel and large area, high speed light shutter, etc. have been expected.

The present inventors have disclosed the following compounds having two adjacent rings at the central part thereof:

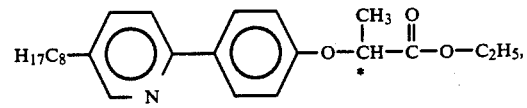

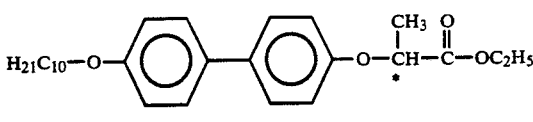

and

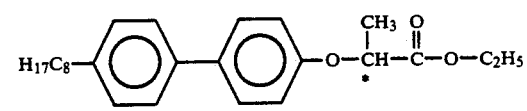

(Japanese patent application laid-open No. Hei 1-128598/ 1989). However, all of these compounds exhibit only melting points as phase transition points. Further, even in the case that these compounds are added to achiral smectic C liquid crystal compositions, the induced ferroelectric mesomorphic ranges are far inferior to those prior to the addition. Thus, improvement of the compounds has been desired.

SUMMARY OF THE INVENTION

The object of the present invention is to provide an optically active compound useful as a constituent of the above ferroelectric liquid crystal compositions and a ferroelectric liquid crystal composition containing the above compound.

As described above with regard to the prior art, the ferroelectric liquid crystal display mode has a possibility of exhibiting superior characteristics. However, the mode has not yet reached practical use, because compounds having a sufficiently large spontaneous polarization value Ps and a broad operation temperature range have not yet been found.

Accordingly, another object of the present invention is to provide a compound having a large Ps value, particularly for realizing a high speed response.

The present invention resides in:

an optically active 2,5-diphenylpyrimidine compound expressed by the formula

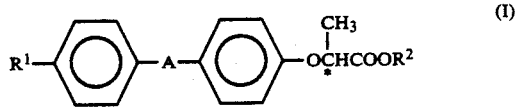

wherein $R^1$ represents an alkyl group or an alkoxy group each of 1 to 20 carbon atoms, $R^2$ represents an alkyl group of 1 to 20 carbon atoms, A represents

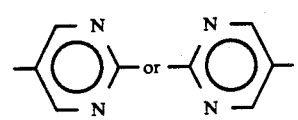

and the symbol * indicates that the carbon atom onto which the symbol is attached is an asymmetric one, and a liquid crystal composition containing the compound.

DETAILED DESCRIPTION OF PREFERRED EMBODIMENTS

In the above formula (I), $R^1$ is preferred to be a linear chain alkyl group or alkoxy group each of 4 to 12 carbon atoms, preferably 6 to 10 carbon atoms, and $R^2$ is preferred to be a linear or branched chain alkyl group of 1 to 10 carbon atoms, preferably 1 to 6 carbon atoms. In the case of a branched chain, it may be an optically active group.

Concrete examples of the compound of the present invention are as follows:

Methyl 2-(4-(2-(4-butylphenyl)pyrimidin-5-yl)-phenoxy)propionate
Ethyl 2-(4-(2-(4-butylphenyl)pyrimidin-5-yl)-phenoxy)propionate
Propyl 2-(4-(2-(4-butylphenyl)pyrimidin-5-yl)-phenoxy)propionate
Butyl 2-(4-(2-(4-butylphenyl)pyrimidin-5- yl)phenoxy)propionate
Pentyl 2-(4-(2-(4-butylphenyl)pyrimidin-5-yl)-phenoxy)propionate
Hexyl 2-(4-(2-(4-butylphenyl)pyrimidin-5- yl)-phenoxy)propionate
Methyl 2-(4-(2-(4-pentylphenyl)pyrimidin-5-yl)-phenoxy)propionate
Ethyl 2-(4-(2-(4-pentylphenyl)pyrimidin-5-yl)-phenoxy)propionate
Propyl 2-(4-(2-(4-pentylphenyl)pyrimidin-5-yl)-phenoxy)propionate
Butyl 2-(4-(2-(4-pentylphenyl)pyrimidin-5-yl)-phenoxy)propionate
Pentyl 2-(4-(2-(4-pentylphenyl)pyrimidin-5-yl)-phenoxy)propionate
Hexyl 2-(4-(2-(4-pentylphenyl)pyrimidin-5-yl)-phenoxy),propionate
Methyl 2-(4-(2-(4-hexylphenyl)pyrimidin-5-yl)-phenoxy)propionate
Ethyl 2-(4-(2-(4-hexylphenyl)pyrimidin-5- yl)-phenoxy)propionate
Propyl 2-(4-(2-(4-hexylphenyl)pyrimidin-5-yl)-phenoxy)propionate
Butyl 2-(4-(2-(4-hexylphenyl)pyrimidin-5- yl)-phenoxy)propionate
Pentyl 2-(4-(2-(4-hexylphenyl)pyrimidin-5-yl)-phenoxy)propionate
Hexyl 2-(4-(2-(4-hexylphenyl)pyrimidin-5- yl)-phenoxy)propionate
Methyl 2-(4-(2-(4-heptylphenyl)pyrimidin-5-yl)-phenoxy)propionate
Ethyl 2-(4-(2-(4-heptylphenyl)pyrimidin-5-yl)-phenoxy)propionate
Propyl 2-(4-(2-(4-heptylphenyl)pyrimidin-5-yl)-phenoxy)propionate
Butyl 2-(4-(2-(4-heptylphenyl)pyrimidin-5-yl)-phenoxy)propionate
Pentyl 2-(4-(2-(4-heptylphenyl)pyrimidin-5-yl)-phenoxy)propionate
Hexyl 2-(4-(2-(4-heptylphenyl)pyrimidin-5-yl)-phenoxy)propionate
Methyl 2-(4-(2-(4-octylphenyl)pyrimidin-5-yl)-phenoxy)propionate
Ethyl 2-(4-(2-(4-octylphenyl)pyrimidin-5-yl)-phenoxy)-propionate
Propyl 2-(4-(2-(4-octylphenyl)pyrimidin-5-yl)-phenoxy)propionate
Butyl 2-(4-(2-(4-octylphenyl)pyrimidin-5-yl)-phenoxy)-propionate
Pentyl 2-(4-(2-(4-octylphenyl)pyrimidin-5-yl)-phenoxy)propionate
Hexyl 2-(4-(2-(4-octylphenyl)pyrimidin-5-yl)-phenoxy)-propionate
Methyl 2-(4-(2-(4-nonylphenyl)pyrimidin-5-yl)-phenoxy)propionate
Ethyl 2-(4-(2-(4-nonylphenyl)pyrimidin-5-yl)-phenoxy)propionate
Propyl 2-(4-(2-(4-nonylphenyl)pyrimidin-5-yl)-phenoxy)propionate
Butyl 2-(4-(2-(4-nonylphenyl)pyrimidin-5-yl)-phenoxy)-propionate
Pentyl 2-(4-(2-(4-nonylphenyl)pyrimidin-5-yl)-phenoxy)propionate
Hexyl 2-(4-(2-(4-nonylphenyl)pyrimidin-5-yl)-phenoxy)propionate
Methyl 2-(4-(2-(4-decylphenyl)pyrimidin-5-yl)-phenoxy)propionate
Ethyl 2-(4-(2-(4-decylphenyl)pyrimidin-5-yl)-phenoxy),propionate
Propyl 2-(4-(2-(4-decylphenyl)pyrimidin-5-yl)-phenoxy)propionate
Butyl 2-(4-(2-(4-decylphenyl)pyrimidin-5-yl)-phenoxy)propionate
Pentyl 2-(4-(2-(4-decylphenyl)pyrimidin-5-yl)-phenoxy)propionate
Hexyl 2-(4-(2-(4-decylphenyl)pyrimidin-5-yl)-phenoxy)propionate
Methyl 2-(4-(2-(4-undecylphenyl)pyrimidin-5-yl)-phenoxy)propionate
Ethyl 2-(4-(2-(4-undecylphenyl)pyrimidin-5-yl)-phenoxy)propionate
Propyl 2-(4-(2-(4-undecylphenyl)pyrimidin-5-yl)-phenoxy)propionate
Butyl 2-(4-(2-(4-undecylphenyl)pyrimidin-5-yl)-phenoxy)propionate
Pentyl 2-(4-(2-(4-undecylphenyl)pyrimidin-5-yl)-phenoxy)propionate
Hexyl 2-(4-(2-(4-undecylphenyl)pyrimidin-5-yl)-phenoxy)propionate
Methyl 2-(4-(2-(4-dodecylphenyl)pyrimidin-5-yl)-phenoxy)propionate
Ethyl 2-(4-(2-(4-dodecylphenyl)pyrimidin-5-yl)-phenoxy)propionate
Propyl 2-(4-(2-(4-dodecylphenyl)pyrimidin-5-yl)-phenoxy)propionate
Butyl 2-(4-(2-(4-dodecylphenyl)pyrimidin-5-yl)-phenoxy)propionate
Pentyl 2-(4-(2-(4-dodecylphenyl)pyrimidin-5-yl)-phenoxy)propionate
Hexyl 2-(4-(2-(4-dodecylphenyl)pyrimdin-5-yl)-phenoxy)propionate
Methyl 2-(4-(5-(4-butylphenyl)pyrimidin-2-yl)-phenoxy)propionate
Ethyl 2-(4-(5-(4-butylphenyl)pyrimidin-2-yl)-phenoxy)-propionate
Propyl 2-(4-(5-(4-butylphenyl)pyrimidin-2-yl)-phenoxy)propionate
Butyl 2-(4-(5-(4-butylphenyl)pyrimidin-2-yl)-phenoxy)-propionate
Pentyl 2-(4-(5-(4-butylphenyl)pyrimidin-2-yl)-phenoxy)propionate
Hexyl 2-(4-(5-(4-butylphenyl)pyrimidin-2-yl)-phenoxy)-propionate
Methyl 2-(4-(5-(4-pentylphenyl)pyrimidin-2-yl)-phenoxy)propionate
Ethyl 2-(4-(5-(4-pentylphenyl)pyrimdin-2-yl)-phenoxy)propionate Propyl 2-(4-(5-(4-pentylphenyl)pyrimidin-2-yl)-phenoxy)propionate
Butyl 2-(4-(5-(4-pentylphenyl)pyrimidin-2-yl)-phenoxy)propionate
Pentyl 2-(4-(5-(4-pentylphenyl)pyrimidin-2-yl)-phenoxy)propionate
Hexyl 2-(4-(5-(4-pentylphenyl)pyrimidin-2-yl)-phenoxy)propionate
Methyl 2-(4-(5-(4-hexylphenyl)pyrimidin-2-yl)-phenoxy)propionate
Ethyl 2-(4-(5-(4-hexylphenyl)pyrimidin-2-yl)-phenoxy)propionate
Propyl 2-(4-(5-(4-hexylphenyl)pyrimidin-2-yl)-phenoxy)propionate
Butyl 2-(4-(5-(4-hexylphenyl)pyrimidin-2-yl)-phenoxy)propionate
Pentyl 2-(4-(5-(4-hexylphenyl)pyrimidin-2-yl)-phenoxy)propionate
Hexyl 2-(4-(5-(4-hexylphenyl)pyrimidin-2-yl)-phenoxy)propionate
Methyl 2-(4-(5-(4-heptylphenyl)pyrimidin-2-yl)-phenoxy)propionate
Ethyl 2-(4-(5-(4-heptylphenyl)pyrimidin-2-yl)-phenoxy)propionate
Propyl 2-(4-(5-(4-heptylphenyl)pyrimidin-2-yl)-phenoxy)propionate
Butyl 2-(4-(5-(4-heptylphenyl)pyrimidin-2-yl)-phenoxy)propionate
Pentyl 2-(4-(5-(4-heptylphenyl)pyrimidin-2-yl)-phenoxy)propionate
Hexyl 2-(4-(5-(4-heptylphenyl)pyrimidin-2-yl)-phenoxy)propionate
Methyl 2-(4-(5-(4-octylphenyl)pyrimidin-2-yl)-phenoxy)propionate
Ethyl 2-(4-(5-(4-octylphenyl)pyrimidin-2-yl)-phenoxy)propionate
Propyl 2-(4-(5-(4-octylphenyl)pyrimidin-2-yl)-phenoxy)propionate
Butyl 2-(4-(5-(4-octylphenyl)pyrimidin-2-yl)-phenoxy)propionate
Pentyl 2-(4-(5-(4-octylphenyl)pyrimidin-2-yl)-phenoxy)propionate
Hexyl 2-(4-(5-(4-octylphenyl)pyrimidin-2-yl)-phenoxy)propionate
Methyl 2-(4-(5-(4-nonylphenyl)pyrimidin-2-yl)-phenoxy)propionate
Ethyl 2-(4-(5-(4-nonylphenyl)pyrimidin-2-yl)-phenoxy)propionate
Propyl 2-(4-(5-(4-nonylphenyl)pyrimidin-2-yl)-phenoxy)propionate
Butyl 2-(4-(5-(4-nonylphenyl)pyrimidin-2-yl)-phenoxy)propionate
Pentyl 2-(4-(5-(4-nonylphenyl)pyrimidin-2-yl)-phenoxy)propionate
Hexyl 2-(4-(5-(4-nonylphenyl)pyrimidin-2-yl)-phenoxy)propionate
Methyl 2-(4-(5-(4-decylphenyl)pyrimidin-2-yl)-phenoxy)propionate
Ethyl 2-(4-(5-(4-decylphenyl)pyrimidin-2-yl)-phenoxy)propionate
Propyl 2-(4-(5-(4-decylphenyl)pyrimidin-2-yl)-phenoxy)propionate
Butyl 2-(4-(5-(4-decylphenyl)pyrimidin-2-yl)-phenoxy)propionate
Pentyl 2-(4-(5-(4-decylphenyl)pyrimidin-2-yl)-phenoxy)propionate
Hexyl 2-(4-(5-(4-decylphenyl)pyrimidin-2-yl)-phenoxy)propionate
Methyl 2-(4-(5-(4-undecylphenyl)pyrimidin-2-yl)-phenoxy)propionate
Ethyl 2-(4-(5-(4-undecylphenyl)pyrimidin-2-yl)-phenoxy)propionate
Propyl 2-(4-(5-(4-undecylphenyl)pyrimidin-2-yl)-phenoxy)propionate
Butyl 2-(4-(5-(4-undecylphenyl)pyrimidin-2-yl)-phenoxy)propionate
Pentyl 2-(4-(5-(4-undecylphenyl)pyrimidin-2-yl)-phenoxy)propionate
Hexyl 2-(4-(5-(4-undecylphenyl)pyrimidin-2-yl)-phenoxy)propionate
Methyl 2-(4-(5-(4-dodecylphenyl)pyrimidin-2-yl)-phenoxy)propionate
Ethyl 2-(4-(5-(4-dodecylphenyl)pyrimidin-2-yl)-phenoxy)propionate
Propyl 2-(4-(5-(4-dodecylphenyl)pyrimidin-2-yl)-phenoxy)propionate
Butyl 2-(4-(5-(4-dodecylphenyl)pyrimidin-2-yl)-phenoxy)propionate
Pentyl 2-(4-(5-(4-dodecylphenyl)pyrimidin-2-yl)-phenoxy)propionate
Hexyl 2-(4-(5-(4-dodecylphenyl)pyrimidin-2-yl)-phenoxy)propionate The compound of the present invention has a notable characteristic that it has a core of three rings consisting of three six-membered rings, but has no bonding group inside the core such as ester bond, ethane bond, methyleneoxy bond, azomethine bond, azo bond, azoxy bond, etc. This structural characteristic exhibits various good effects.

Further, the compound of the present invention is liable to exhibit a liquid crystalline state by itself, and even in the case that no liquid crystalline state is exhibited by itself, even when it is added to achiral smectic C liquid crystal compositions, the induced ferroelectric mesomorphic range is not so inferior to that prior to its addition.

The compound of the present invention has a function of increasing the spontaneous polarization value Ps as one of the important physical properties of ferroelectric liquid crystal materials. Even in the case that the compound of the present invention, when solely used, exhibits no ferroelectric liquid crystalline phase, if the compound is added as a component of a ferroelectric liquid crystal composition, a large Ps value is exhibited in the resulting composition. In ferroelectric liquid crystal display devices, the response time is proportional to Ps value. A large Ps value means an enhanced possibility of affording a display element having a high speed response. The compound of the present invention as mentioned later, when solely used, exhibits no ferroelectric liquid crystalline phase, but when it was added in an amount of 20% by weight to an achiral smectic liquid crystal composition, the resulting liquid crystal composition exhibited a Ps value at 25° C. as very large as 26.3 nC/cm$^2$ (131.5 nC/cm$^2$ when extrapolated to 100% of the compound).

Further, the compound of the present invention has a low viscosity, and due to a synergistic effect of the low viscosity and its large Ps value, it is possible to exhibit high speed response properties.

Further, since the compound of the present invention is optically active, its addition to a nematic liquid crystal makes it possible to induce a twist structure. Since a nematic liquid crystal having a twist structure, i.e. a chiral nematic liquid crystal, shows no reverse twist domain (dechiralization lines) in a TN mode display device, it is possible to utilize the crystal as a preventive agent therefor.

Further, a chiral nematic liquid crystal consisting of the compound of the present invention has a short pitch; hence its addition in a small quantity makes it possible to obtain a required pitch length, and accordingly the compound is also useful as a pitch-adjusting agent.

The compound of the present invention will be described in more detail by way of Examples, but it should not be construed to be limited thereto.

EXAMPLE 1

Preparation of ethyl R-2-{4-[2-(4-nonylphenyl)-pyrimidin-5-yl]phenoxy} propionate (a compound of the formula (I) wherein

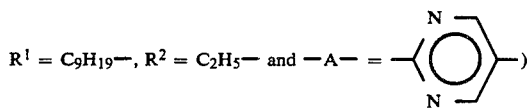

The first step

Preparation of 5-(4-methoxyphenyl)-2-(4-nonylphenyl)-pyrimidine

Phosphorus oxychloride (184 g) was dropwisely added to dimethylformamide (146 g), followed by adding p-methoxyphenylacetic acid (66 g) little by little at −10° C., agitating the reaction solution at 20° C. for one hour, further at 60° C. for 2 hours and further at 80° C. for 5 hours, distilling off dimethylformamide in vacuo, cooling the residue, pouring it into a saturated aqueous solution of magnesium perchlorate, filtering off deposited crystals and washing with ether to obtain a salt (67 g) (m.p.: 133.3–134.4° C.).

A mixture of this salt (60 g), p-nonylbenzamidine hydrochloride (48 g), sodium methoxide (13.6 g) and ethanol (600 ml) was refluxed for 6 hours, followed by adding toluene, washing with an alkali and further with water, distilling off the solvent and recrystallizing the residue from a mixed solvent of ethanol with ethyl acetate to obtain 5-(4-methoxyphenyl)-2-(4-nonylphenyl)-pyrimidine (60 g). This product exhibited a C-SA point of 88.9° C., a SA-N point of 186.0° C. and a N-I point of 194.4° C.

The second step

Preparation of 5-(4-hydroxyphenyl)-2-(4-nonylphenyl)-pyrimidine

A mixture of 5-(4-methoxyphenyl)-2-(4-nonylphenyl)-pyrimidine (60 g), hydrobromic acid (240 g) and acetic acid (1 l) was refluxed for 40 hours, followed by distilling off most part of the acetic acid, pouring the residue into 2N-NaOH aqueous solution and recrystallizing the deposited crystals from ethyl acetate to obtain 5-(4-hydroxyphenyl)-2-(4-nonylphenyl)pyrimidine (32.6 g). This product had a C-SA point of 98.4° C. and a SA-I point of 138.6° C.

The third step

Preparation of ethyl R-2-{4-[2-(4-nonylphenyl)-pyrimidin-5-yl]phenoxy}propionate A mixture of 5-(4-hydroxyphenyl)-2-(4-nonylphenyl)pyrimidine (2.0 g), ethyl S-2-methanesulfonyloxypropionate (1.1 g), potassium carbonate (0.9 g), acetonitrile (50 ml) and dimethylsulfoxide (25 ml) was agitated at 60° C. for 5 hours, followed by adding toluene (300 ml) and further water (150 ml) to terminate the reaction, separating the resulting organic layer, washing with an acid, washing with an alkali and washing with water, drying, concentrating, purifying according to column chromatography using toluene as an eluting solvent and recrystallizing from ethanol to obtain ethyl R-2-{4-[2-(4-nonylphenyl) pyrimidin-5-yl]phenoxy} propionate (1.2 g).

M.P. 82.1° C.

$[\alpha]_D$+23.5 (C 1.0, CHCl₃, t=27° C.)

EXAMPLE 2

Preparation of Ethyl R-2-{4-[5-(4-butylphenyl)-pyrimidin-2-yl]phenoxy}propionate (a compound of the formula (I) wherein

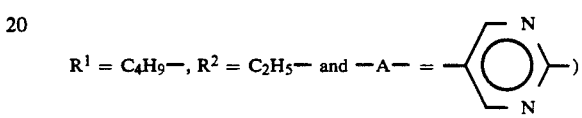

A mixture of 5-(4-butylphenyl)-2-(4-hydroxyphenyl)-pyrimidine (m.p.:172.5–173.3° C. (2.0 g), ethyl S-2- methanesulphonyloxypropionate (1.1 g), potassium carbonate (0.9 g), acetonitrile (50 ml) and dimethyl sulfoxide (25 ml) was agitated at 60° C. for 5 hours, followed by adding toluene (300 ml) and further water (150 ml) to terminate the reaction and purifying the resulting material in the same manner as in Example 1 to obtain ethyl R-2-{4-[5-(4-butylphenyl)pyrimidin-2-yl]phenoxy}propionate (1.0 g).

EXAMPLE 3

Preparation of hexyl R-2-{4-[5-(4-butylphenyl)-pyrimidin-2-yl]phenoxy}propionate (a compound of the formula (I) wherein

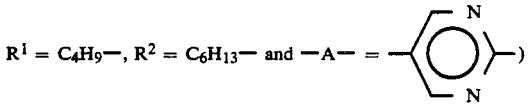

A mixture of ethyl R-2-{4-[5-(4-butylphenyl)-pyrimidin-2-yl]phenoxy}propionate (1.0 g) prepared in Example 2, a 50% aqueous solution of NaOH (3 ml) and ethanol (50 ml) was heated under reflux for 2 hours, followed by adding toluene (100 ml) and 6N-HCl (100 ml), washing the resulting organic layer with water, drying, concentrating, dissolving the residue in dichloromethane (50 ml), adding dicyclohexylcarbodiimide (2 g) and n-hexyl alcohol (1 g), agitating the mixture at room temperature, filtering off the resulting solids, washing the mother liquor with water, an acid, an alkali and water for neutralization in this order and recrystallizing the residue from ethanol to obtain hexyl R-2-{4[5-(4-butylphenyl) pyrimidin-2-yl]phenoxy}propionate.

EXAMPLE 4

(Use example 1)

The following composition A of achiral substances having SC phase was prepared:

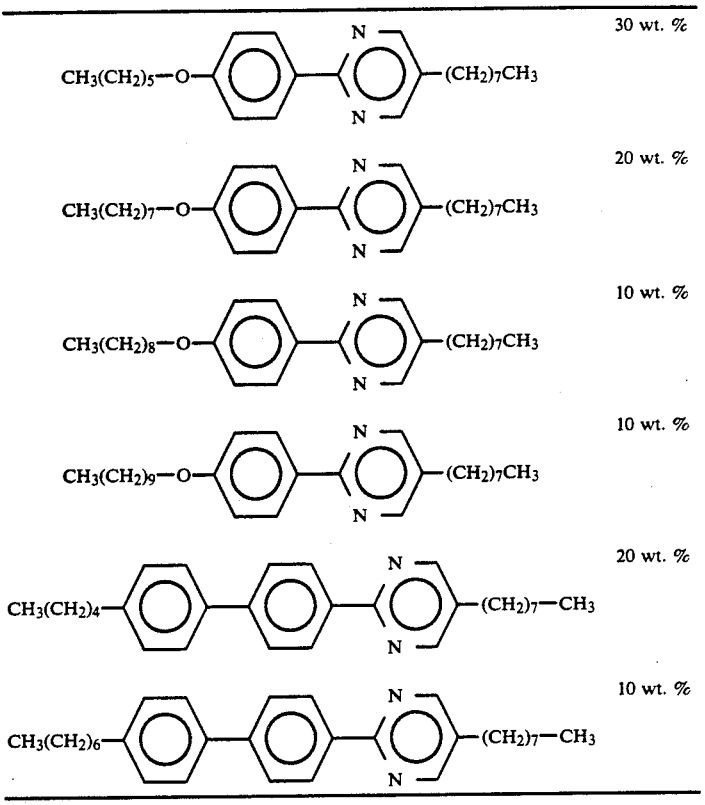

| | |
|---|---|
| | 30 wt. % |
| | 20 wt. % |
| | 10 wt. % |
| | 10 wt. % |
| | 20 wt. % |
| | 10 wt. % |

The composition A exhibited the following phase transition points:

(I: Isotropic phase, N: Nematic phase, SA: Smectic A phase, SC: Smectic C phase, C: Cholesteric phase)

To this composition A was added ethyl R-2-{4-[2 nonylphenyl) pyrimidin-5-yl]phenoxy}propionate in an amount of 20% by weight, which is of the compounds of the present invention (compound of Example 1). As a result, SC* phase exhibiting ferroelectricity at 61.4° C. or lower appeared. The Ps of this composition was measured at various temperatures. The results were as follows:

| Temperature (°C.) | Ps (nC/cm$^2$) |
|---|---|
| 56.4 | 9.4 |
| 51.4 | 13.1 |
| 46.4 | 15.0 |
| 41.4 | 18.8 |
| 31.4 | 23.9 |
| 25 | 26.3 |

EXAMPLE 5

(Use example 2)

A nematic liquid crystal composition consisting of

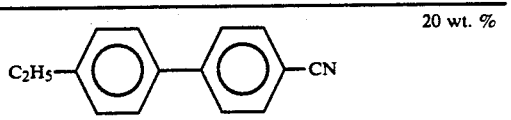     20 wt. %

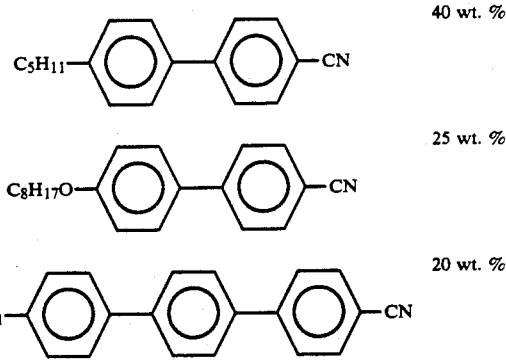

| | |
|---|---|
| | 40 wt. % |
| | 25 wt. % |
| | 20 wt. % | was filled in a cell provided with transparent electrodes each obtained by coating polyvinyl alcohol as an aligning agent thereon and rubbing the resulting surface to subject it to a parallel, aligning treatment, and having a distance of 10 μm between the electrodes to prepare a TN mode display cell, followed by observing the cell under a polarizing microscope. A reverse twist domain was formed. To this nematic liquid crystal composition was added the compound of Example 1 of the present invention in an amount of 0.1% by weight, followed by similarly observing the resulting mixture. As a result, the reverse twist domain disappeared and a uniform mono domain was observed.

EXAMPLE 6

(Use example 3)

To a commercially available nematic liquid crystal composition ZLI 1132 (tradename of Merck Co., Ltd.) was added the compound of Example 1 of the present invention in an amount of 1% weight to prepare a chiral nematic liquid crystal composition, which was then filled in a wedge type cell subjected to a parallel aligning treatment to observe its pitch length. The results were as follows:

| Temperature (°C.) | Pitch length (μm) |
| --- | --- |
| 20 | 10.9 |
| 30 | 11.6 |
| 40 | 12.5 |
| 50 | 12.9 |
| 60 | 13.4 |

COMPARATIVE EXAMPLE 1

(Comparative use example 1)

A compound

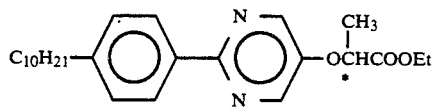

was added in an amount of 20% by weight to the above composition A in the same manner as in Example 4. The resulting composition exhibited the following phase transition points:

Room temperature — SA $\xrightarrow{44.0}$ N* $\xrightarrow{73.4}$ I

COMPARATIVE EXAMPLE 2

(Comparative use example 2)

A compound

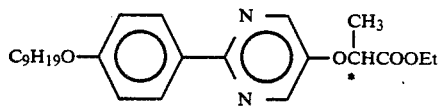

was added in an amount of 20% by weight to the composition A in the same manner as in Example 4. The resulting composition exhibited the following phase transition points:

Cr $\xrightarrow{30.2}$ N* $\xrightarrow{74.5}$ I

As apparent from the above-mentioned Examples, when the compound of the present invention is used as a component of ferroelectric liquid crystal compositions, it is possible to obtain ferroelectric liquid crystal compositions having a large Ps value, and also when the compound is used as a component of nematic liquid crystal compositions, it is possible to impart a twist structure and thereby prevent reverse twist domain from forming.

What we claim is:

1. An optically active 2,5-diphenylpyrimidine compound expressed by the formula

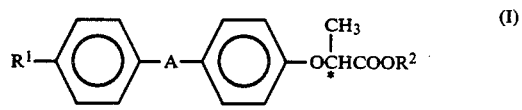

wherein $R^1$ represents an alkyl group or an alkoxy group each of 1 to 20 carbon atoms, $R^2$ represents an alkyl group of 1 to 20 carbon atoms, A represents

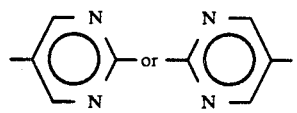

and the symbol * indicates that the carbon atom onto which the symbol is attached is an asymmetric carbon.

2. An optically active compound according to claim 1, wherein said $R^1$ represents an alkyl group or an alkoxy group each of 4 to 12 carbon atoms.

3. An optically active compound according to claim 1, wherein said $R^2$ represents an alkyl group of 1 to 10 carbon atoms.

4. A chiral liquid crystal composition comprising at least two components at least one of which is an optically active compound as set forth in claim 1.

5. A chiral liquid crystal composition according to claim 4, exhibiting a chiral smectic phase.

6. A chiral liquid crystal composition according to claim 4, exhibiting a chiral nematic phase.

7. An electrooptical element using a chiral liquid crystal composition as set forth in claim 4.

* * * * *